United States Patent [19]

Bolesky et al.

[11] Patent Number: 5,370,706
[45] Date of Patent: * Dec. 6, 1994

[54] MODULAR HIP PROSTHESIS

[75] Inventors: Richard Bolesky; Todd S. Smith, both of Warsaw, Ind.

[73] Assignee: Depuy Inc., Warsaw, Ind.

[*] Notice: The portion of the term of this patent subsequent to Jan. 14, 2009 has been disclaimed.

[21] Appl. No.: 105,940

[22] Filed: Aug. 13, 1993

Related U.S. Application Data

[60] Continuation of Ser. No. 891,419, May 29, 1992, Pat. No. 5,286,260, which is a division of Ser. No. 450,058, Dec. 13, 1989, Pat. No. 5,181,928, which is a continuation of Ser. No. 896,857, Aug. 15, 1986, abandoned.

[51] Int. Cl.$^5$ .............................................. A61F 2/24
[52] U.S. Cl. ........................................ 623/18; 623/23; 623/19
[58] Field of Search ..................... 623/16, 18, 19, 20, 623/21, 22, 23

[56] References Cited

U.S. PATENT DOCUMENTS

| | | |
|---|---|---|
| 2,682,265 | 6/1954 | Collison . |
| 2,719,522 | 10/1955 | Hudack . |
| 2,765,787 | 10/1956 | Pellet . |
| 2,781,758 | 2/1957 | Chevalier . |
| 2,785,673 | 3/1957 | Anderson . |
| 3,064,645 | 11/1962 | Ficat et al. . |
| 3,067,740 | 12/1962 | Haboush . |
| 3,102,536 | 9/1963 | Rose et al. . |
| 3,806,957 | 4/1974 | Shersher . |
| 3,818,512 | 6/1974 | Shersher . |
| 3,863,273 | 2/1975 | Averill . |
| 3,918,441 | 11/1975 | Getscher . |
| 3,987,499 | 10/1976 | Scharbach et al. . |
| 4,051,559 | 10/1977 | Pifferi . |

(List continued on next page.)

FOREIGN PATENT DOCUMENTS

| | | | |
|---|---|---|---|
| 0038897 | 11/1981 | European Pat. Off. | ............ 623/23 |
| 0163121A1 | 4/1985 | European Pat. Off. | |
| 0198163A2 | 2/1986 | European Pat. Off. | |
| 0190981A1 | 8/1986 | European Pat. Off. | |
| 2183230 | 12/1973 | France . | |
| 2225141 | 8/1974 | France . | |
| 2378505 | 7/1976 | France . | |
| 2575-383A | 12/1984 | France . | |
| 2576793 | 1/1985 | France . | |
| 2318396 | 4/1973 | Germany . | |
| 3336005 | 4/1983 | Germany . | |
| 3406358 | 2/1984 | Germany . | |
| 1443470 | 7/1976 | United Kingdom . | |
| 1521679 | 8/1978 | United Kingdom . | |
| 1531487 | 11/1978 | United Kingdom . | |
| 2070939 | 9/1981 | United Kingdom . | |
| WO83/02555 | 8/1983 | WIPO . | |

OTHER PUBLICATIONS

Tumorprotheses des Hüftrgelenkes (Indikation und Ergebnisse); By: M. Jäger L. Löffler, D. Kohn.
Concept and Material Properties of a Cementless hip Prosthesis System with Al$_2$O$_3$ Ceramic Ball Heads and Wrought Ti–6A1–4V Stems; By: K. Zweymüller and M. Semlitsch.

Primary Examiner—David Isabella
Attorney, Agent, or Firm—Barnes & Thornburg

[57] ABSTRACT

A modular hip prosthesis for the replacement of a portion of the femur is provided. The prosthesis is assembled from a kit that includes a stem member having an upper portion and a lower portion, with the lower portion sized to be received in the femur. The kit also includes a body member that is sized to replace a portion of the femur and is configured to be received over the upper portion of a stem member. The kit also includes a head member that is sized to replace the head of the femur. A neck member is provided to attach the head member to the body member to form an assembled prosthesis.

23 Claims, 3 Drawing Sheets

U.S. PATENT DOCUMENTS

| | | |
|---|---|---|
| 4,115,875 | 9/1978 | Rambert et al. . |
| 4,404,691 | 9/1983 | Buning et al. . |
| 4,459,708 | 7/1984 | Buttazzoni . |
| 4,488,319 | 12/1984 | von Recüm . |
| 4,520,511 | 6/1985 | Gianezio et al. . |
| 4,532,660 | 8/1985 | Field . |
| 4,578,081 | 3/1986 | Harder et al. . |
| 4,608,055 | 8/1986 | Morrey et al. . |
| 4,655,778 | 4/1987 | Koeneman . |
| 4,676,797 | 6/1987 | Anapliotis et al. . |
| 4,693,724 | 9/1987 | Rhenter et al. . |
| 4,698,063 | 10/1987 | Link et al. . |
| 4,822,370 | 4/1989 | Schelhas . |
| 4,840,632 | 6/1989 | Kampner . |
| 4,842,606 | 6/1989 | Kranz et al. . |
| 4,865,605 | 9/1989 | Dines et al. . |
| 4,963,155 | 10/1990 | Lazzeri et al. . |
| 5,002,581 | 3/1991 | Paxson et al. . |
| 5,080,685 | 1/1992 | Bolesky et al. . |

MODULAR HIP PROSTHESIS

This is a continuation of application Ser. No. 07/891,419, filed May 29, 1992 now U.S. Pat. No. 5,286,260) which is divisional application of Ser. No. 07/450,058, filed Dec. 13, 1989 (now U.S. Pat. No. 5,181,928) which is a continuation of Ser. No. 06/896,857, filed Aug. 15, 1986 (now abandoned).

BACKGROUND AND SUMMARY OF THE INVENTION

The present invention relates to prostheses for replacement of a portion of the hip joint. More particularly, the present invention relates to a modular prosthesis for replacement of the upper portion of the femur.

Conventional prostheses for the replacement of the upper portion of the femur are generally unitary structures. The conventional prosthesis generally includes a stem portion that is designed to extend downwardly into a cavity within the femur. The stem portion may be secured within the femur by the use of bone cement, or in other adaptations, the stem may De configured to promote bone in growth to secure the stem. The conventional hip prosthesis also includes a neck portion that is integral with the stem portion. The neck portion is configured to replace the neck of the femur which will normally be resected with the head of the femur. Integrally fixed to the neck portion will normally be a generally spherical head portion that is configured to replace the head of the femur. A collar may be provided between the neck portion and the stem portion to stabilize the prosthesis on the resected femur. Generally, the collar will rest upon the resected surface of the femur to disperse the load on the prosthesis over a greater area, and to compress the underlying bone. A collar may be provided between the neck portion and the stem portion to stabilize the prosthesis and function as a stop or reference point on the resected femur.

Because conventional prostheses are generally unitary devices, the practice has been to maintain a large inventory of prostheses of different sizes to accommodate the different bone sizes that are to be replaced. Generally, the patient is evaluated by x-ray or some other means to determine the approximate bone size, and consequently the approximate required prosthesis size. During the replacement operation, several different prostheses are made available as suggested by the evaluation. The appropriate prosthesis is then selected for insertion into the patient at the time of operation.

One problem with the conventional, unitary prosthesis is that the hospital has to maintain a large number of differently sized prostheses to accommodate different sizes of bones to be replaced. Generally, a supply of prostheses with and without a collar also must be maintained in the inventory. Also, prostheses with different shapes and angles of the stem and neck portion must be maintained. Even with this large inventory of prostheses, it is often difficult to find a prosthesis that is sized and shaped exactly for the individual patient.

Prostheses having a stem portion and a separate head portion are known. One such prosthesis is shown in U.S. Pat. No. 4,051,559. U.S. Pat. No. 4,051,559 discloses a prosthesis that includes a separate threaded stem portion that is adapted to be screwed into a prepared cavity within the femur. The prosthesis separately comprises a head portion that includes a neck and collar that is adapted to be mated with the stem portion. This prosthesis is not designed to be assembled prior to insertion within the patient. The stem portion must first be screwed into the cavity within the femur. The head portion is then attached to the installed stem portion by a bolt. The collar is designed to rest upon the resected surface of the femur to support the load placed on the prosthesis. Because of the design of the stem portion, the head portion must include the collar in order to support the weight that will be placed on the prosthesis. This prosthesis is limited in flexibility because the stem portion must be straight in order to be screwed into the femur. Also, the head portion, including the neck and collar is a unitary structure which further reduces the flexibility of the device.

Another prosthesis having a stem portion and a separate head portion is shown in U.S. Pat. No. 3,806,957. U.S. Pat. No. 3,806,957 discloses a prosthesis that includes a separate stem portion having a proximal end that is broadened somewhat. The broadened proximal end of the stem is configured to receive a head and threaded neck portion to form a complete prosthesis. The patent discloses that the neck may be elongated or shortened depending on the specific anatomy of different patients. This prosthesis, like the prosthesis disclosed in U.S. Pat. No. 4,051,559, is limited in flexibility because the head and neck portion is a unitary structure, and because the head and neck portion attaches directly into the stem portion.

A prosthesis in which the stem portion comprises more than one component is shown in U.S. Pat. No. 3,987,499. U.S. Pat. No. 3,987,499 discloses a prosthesis having a stem or shank component that includes two parts, an anchoring part and a transition part. A ball is connected to the transition part. Also, a collar may be included between the ball and a portion of the femur. The anchoring part is provided with external threads that are adapted to tap themselves into the femur. The transition part is coupled to the anchoring part by a guide pin and securing screw. The ball is adapted to be screwed onto the free end of the transition part. One problem with the prosthesis disclosed in U.S. Pat. No. 3,987,499 is that the prosthesis is designed to be placed in position within the body component by component, and assembled sequentially. Another problem with this prosthesis is that the neck is a part of the transition part, which reduces the flexibility of the device. In addition, the collar is configured to be supported only between the bone and the ball, and is thus subject to rotational and toggling instability.

One object of the present invention is to provide a modular hip prosthesis that has a great deal of flexibility in its assembly, both as to the size and shape of the assembled device.

Another object of the present invention is to provide a modular hip prosthesis that may be assembled in the operating room before any component is inserted into the patient.

Yet another object of the present invention is to provide a modular hip prosthesis that is configured to function with or without a collar.

Yet another object of the present invention is to provide a modular hip prosthesis that includes a stem portion that may be shaped to fit a curvature within the bone structure, if necessary.

According to the present invention, a kit for the assembly of a hip prosthesis for the replacement of a portion of a femur is provided. The kit comprises a stem member having an upper portion and a lower portion, with the lower portion sized to be received into the femur. The kit also comprises a body member that is sized to replace a portion of the femur and is configured to be received over the upper portion of the stem member. The kit also comprises a head member that is sized to replace the head of the femur, including means to attach the head member to the body member.

One feature of the present invention is that the kit preferably consists of stem members, body members, and head members, and attaching means all of various sizes and shapes. These separate components are adapted to be assembled together to form a custom prosthesis of a desired size and shape. One advantage of this feature is that a hip prosthesis of a desired size and shape may be assembled from the kit at the time of the operation.

Another feature of the present invention is that the kit comprises body members that are inserted over the stem members and are configured to bear a portion of the load that is exerted on the prosthesis. One advantage of this feature is that the prosthesis may be assembled without a collar component if the indications presented during the operation suggest that a collar may not be needed, or may produce unsatisfactory side effects.

In preferred embodiments of the present invention, the stem member, body member, and the head member are selected from a group consisting of differently sized and shaped members, respectively. One feature of the foregoing structure is that with different sizes and shapes of stem members, body members, and head members, the number of combinations available to assemble a hip prosthesis is greatly increased, without increasing the number of inventoried components. One advantage of this feature is that the flexibility of assembling a hip prosthesis for an individual patient is greatly increased.

Also in preferred embodiments of the present invention, the attaching means involves a neck member that is adapted to be rigidly attached to the body member and to the head member. The neck member is configured to replace the natural neck of the femur. The neck member, like the stem member, body member, and head member, is selected from a group consisting of differently sized neck members to increase the flexibility of the prosthesis.

The modular hip prosthesis of the present invention thus provides the ability to assemble a custom prosthesis by selecting different sizes and shapes of individual components to meet the requirements of the individual patient exactly. The provision of the kit concept for the prosthesis greatly reduces the inventory required to be maintained by the hospital. Also, the kit form of the prosthesis increases greatly the flexibility of the system, and provides for the assembly of a prosthesis that may otherwise be unavailable.

Additional objects, features, and advantages of the invention will be apparent to those skilled in the art upon consideration of the following detailed description of preferred embodiments exemplifying the best mode of carrying out the invention as presently perceived.

BRIEF DESCRIPTION OF THE DRAWINGS

The detailed description particularly refers to the accompanying figures in which.

DETAILED DESCRIPTION OF THE DRAWINGS

Figure 1:
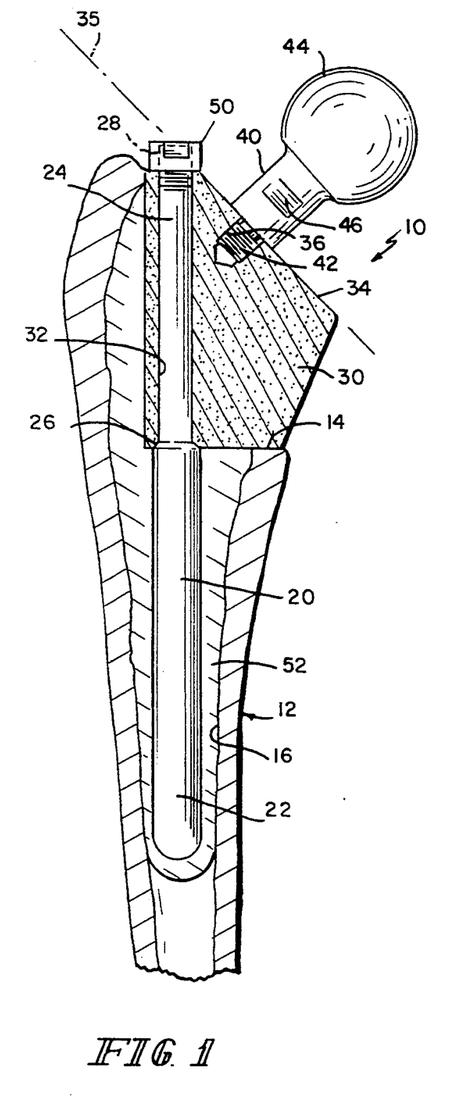
FIG. 1 is a cross sectional view through one embodiment of the modular hip prosthesis of the present invention installed in a femur.

Referring now to FIG. 1, FIG. 1 shows a modular hip prosthesis 10 of the present invention inserted into a femur 12 in which the head and neck portions (not shown) have been resected, The resection of the head and neck portions of the femur 12 has been performed to leave a generally planar surface 14 on the femur 12, A cavity 16 has been formed in the femur 12 to receive the prosthesis 10. It will be understood that the resection procedure and the procedure for forming the cavity are well known in the art. It will also be understood that the cavity 16 may be formed to be the exact same size as the prosthesis 10, or if necessary, the cavity 16 may be formed to be somewhat larger than the size of the prosthesis 10. The cavity 16 shown in FIG. 1 is illustrative of the latter, with the cavity 16 being somewhat larger than the size of the prosthesis 10.

The prosthesis 10 includes an elongated stem member 20 that is generally circular in cross section and includes a lower portion 22 and an upper portion 24. The upper portion 24 has a diameter slightly less than the diameter of the lower portion 22. The demarcation between the upper portion 24 and the lower 22 is marked by a chamfer 26. The upper extremity of the stem member 20 terminates in a threaded end 28. The lower portion 22 may have any of several surface treatments, including, but not limited to, blasted, smooth, porous bony-in growth, and coated.

A body member 30 is shown disposed over the upper portion 24 of the stem member 20, with the upper portion 24 extending through a bore 32 in the body member 30. The body member 30 includes an upwardly and inwardly (medially) facing surface 34 in which a threaded bore 36 has been formed. The surface 34 defines a plane 35 that is generally coincident with a plane defined by the base of the neck (not shown) that has been resected from the femur. The body member 30 may be formed by casting or machining and may have any of the several outer finishes discussed in connection with lower portion 22 of the stem member 20. It will be appreciated that, in the orthopedic implant art, having parts which can be made using machining techniques rather than casting techniques provides significant advantages.

A neck member 40 which replaces the natural neck of the femur (not shown) extends generally upwardly and inwardly from the surface 34. The neck member 40 includes a threaded projection 42 that engages the threaded bore 36 in the body member 30. A head member 44 is formed on the proximal end of the neck member 40, with the head member 44 replacing the natural head of the femur (not shown). Notches 46 are formed in the surface of the neck member to permit a wrench (not shown) to be used to tighten the neck member 40 into the body member 30.

The prosthesis 10 is assembled by first inserting the upper portion 24 of the stem member 20 through the bore 32 in the body member 30. A nut 50 is then engaged with the threaded end 28 of the stem member 20 to secure the stem member 20 to the body member 30. It will be understood that the distal end of the bore 32 in the body member 30 includes a chamfer to mate with the chamfer 26 on the stem member 20 to provide a secure engagement. The neck member 40 is then installed in the body member 30 by engaging the threaded projection 42 with the threaded bore 36. The neck member 40 is then tightened using a wrench (not shown) in the notches 46.

To install the assembled prosthesis 10 in the femur 12, a grouting material 52, or bone cement material, is first injected into the cavity 16. The prosthesis 10 is then placed in the cavity 16 such that the distal end of the body member 30 rests upon the surface 14, and the lower portion 22 of a stem member 20 extends downwardly into the cavity 16. The grouting material 52 surrounds the lower portion 22 of the stem 20 and in some cases a portion of the body member 30 and acts in a known manner to secure the prosthesis 10 within the femur 12.

Figure 2:
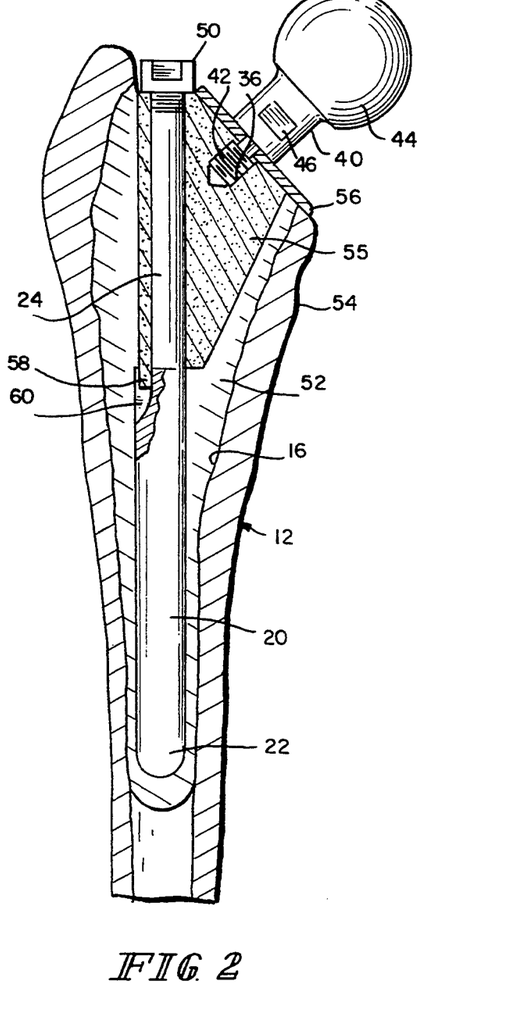
FIG. 2 is a view similar to FIG. 1 showing another embodiment of the present invention.

FIG. 2 shows another embodiment of the present invention that is configured to fulfill slightly different anatomical requirements that may be indicated during the replacement procedure. This embodiment is configured to replace a portion of the femur 12 in which only the head and neck portions (not shown) have been resected. The Calcar portion 54 of the femur 12 has been left intact. Therefore, a smaller body member 55 is shown that can be disposed totally within the cavity 16 in the femur 12. Also, a collar 56 is provided that mates with the body member 55 and extends over the Calcar portion 54 of the femur 12. The collar 56 is provided to distribute the load between the body member 55 and the Calcar portion 54. In this embodiment, the body member 55 includes a key 58 that is received in a keyway 60 that is formed in the stem 20. The key 58 and keyway 60 cooperate to prevent any rotation of the body member 55 with respect to the stem member 20. The prosthesis 10 shown in FIG. 2 is inserted into the cavity 16 of the femur 12 that has been filled with a grouting material 52 to secure the prosthesis 10 in a known manner.

Figure 2A:
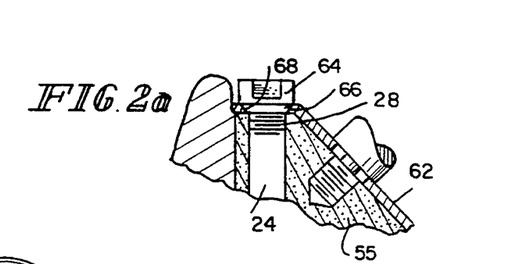
FIG. 2a is a partial view of a modification of the collar component and nut arrangement of the embodiment shown in FIG. 2.

FIG. 2a shows a modification of the embodiment shown in FIG. 2. Specifically, the collar 56 of FIG. 2 is replaced by a collar 62 that extends over the threaded end 28 of the stem member 20. A chamfered hole 66 is formed in the extension of the collar 62 that receives the threaded end 28 of the stem member 20. A nut 64 with a chamfer 68 is provided to engage the threaded end 28 of the stem member 20 with the chamfer 68 of the nut engaging the chamfered hole 66 of the collar 62. The chamfer 68, 66 cooperate to securely engage the collar 62 between the body member 55 and the nut 64.

Figures 3, 4, 5, 6:
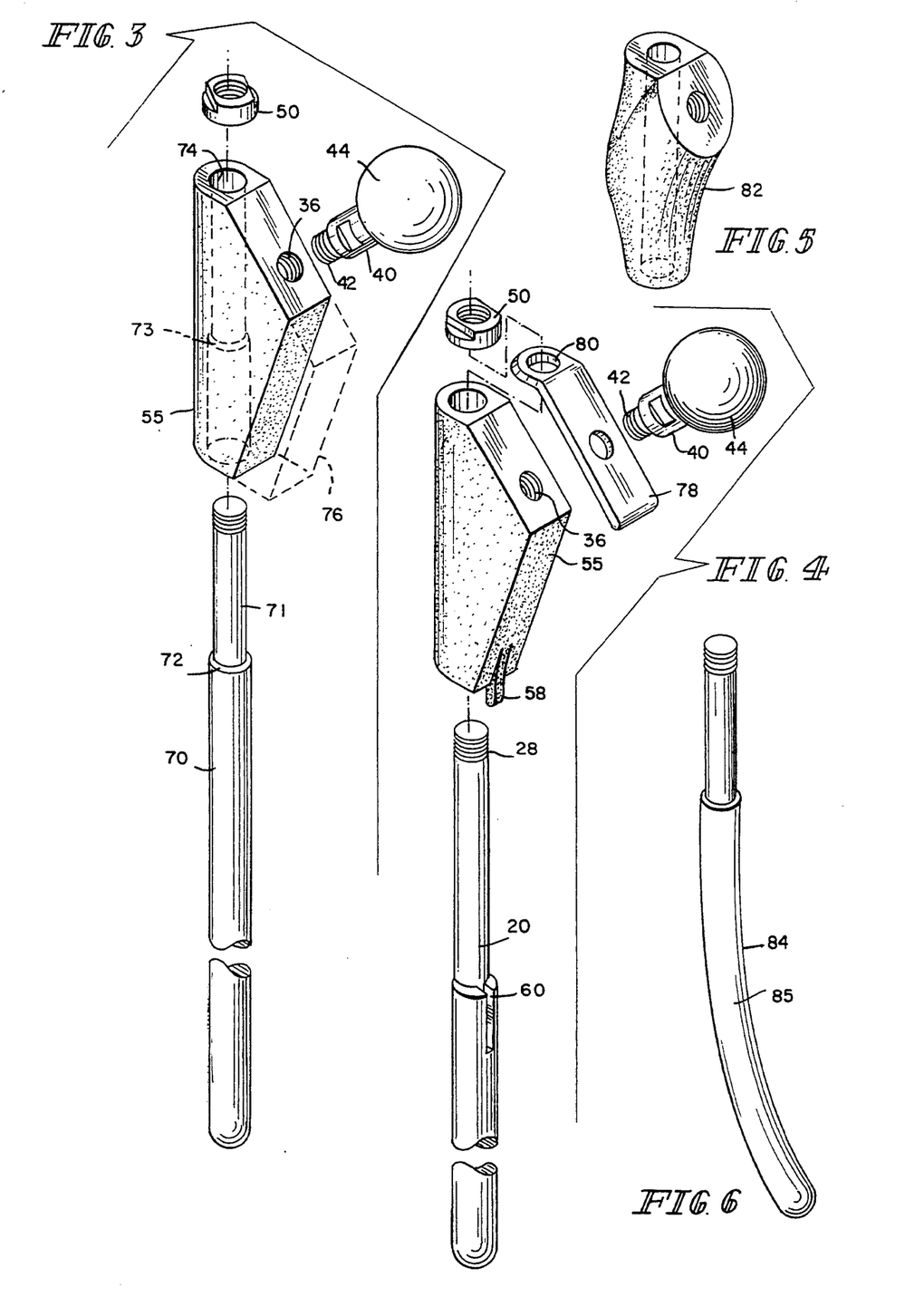
FIG. 3 is an exploded perspective view of another embodiment of the present invention showing a modified stem member and body member.
FIG. 4 is a view similar to FIG. 3 showing another embodiment of the present invention with a collar component and an interlocking key and keyway in the body member and stem member.
FIG. 5 is a perspective view of another embodiment of the present invention showing a modified body member.
FIG. 6 is a perspective view of another embodiment of the present invention showing a modified stem member.

FIG. 3 shows another embodiment of the present invention including a slightly modified stem member 70 that engages the body member 55 of the embodiment shown in FIG. 2. Specifically, the stem member 70 includes a shorter upper portion 71 in comparison to the stem member 20. A chamfer 72 is provided between the upper portion 71 and the main portion of the stem member 70. The body member 55 includes a modified bore 74 extending therethrough to receive the stem member 70. The modified bore 74 has a chamfer 73 to mate with the chamfer 72 on the stem member 70. This modified stem member 70 and body member 55 may be used when additional strength in the stem member 70 is required, such as, for example, when the stem member 70 has a diameter smaller than normal. FIG. 3 also shows an extension 76 (shown only in dotted) that may be added to the body member 55 to make the body member 55 similar to the body member 30 shown in FIG. 1. The extension 76 will be required if the Calcar portion 54 (FIG. 2) of the femur 12 is being resected and replaced.

FIG. 4 shows another embodiment of the present invention similar to the embodiment shown in FIGS. 2 and 2a. In the embodiment shown in FIG. 4, the key 58 on the body portion 55 and the keyway 60 on the stem member 20 are located on the opposite side compared to the embodiment shown in FIG. 2. Also, the collar 78 is similar to the collar 62 shown in FIG. 2a, however the hole 80 in the extension does not contain a chamfer, thereby permitting the use of the unchamfered nut 50 to engage the threaded end 28 of the stem member 20.

FIG. 5 shows another embodiment of the present invention in which a body member 82 is formed in a somewhat irregular shape. The irregular shaped body 82 may be preferable for insertion into certain femurs (not shown). It will be understood that the body member 82 may be a cast material, or may be machined in a known manner and may have a surface treatment similar to that described in relation to the body member 30 (FIG. 1).

FIG. 6 shows another embodiment of the present invention having a modified stem member 84. Specifically, the stem member 84 includes a curved lower portion 85 that may be inserted into the cavity 16 in the femur 12 (not shown) when the anatomical indications so dictate. It will be understood that the stem member 84 may be mated with either the body member 30, the body member 55, or the body member 82, as discussed previously.

Figures 7, 7A, 7B, 7C, 8:
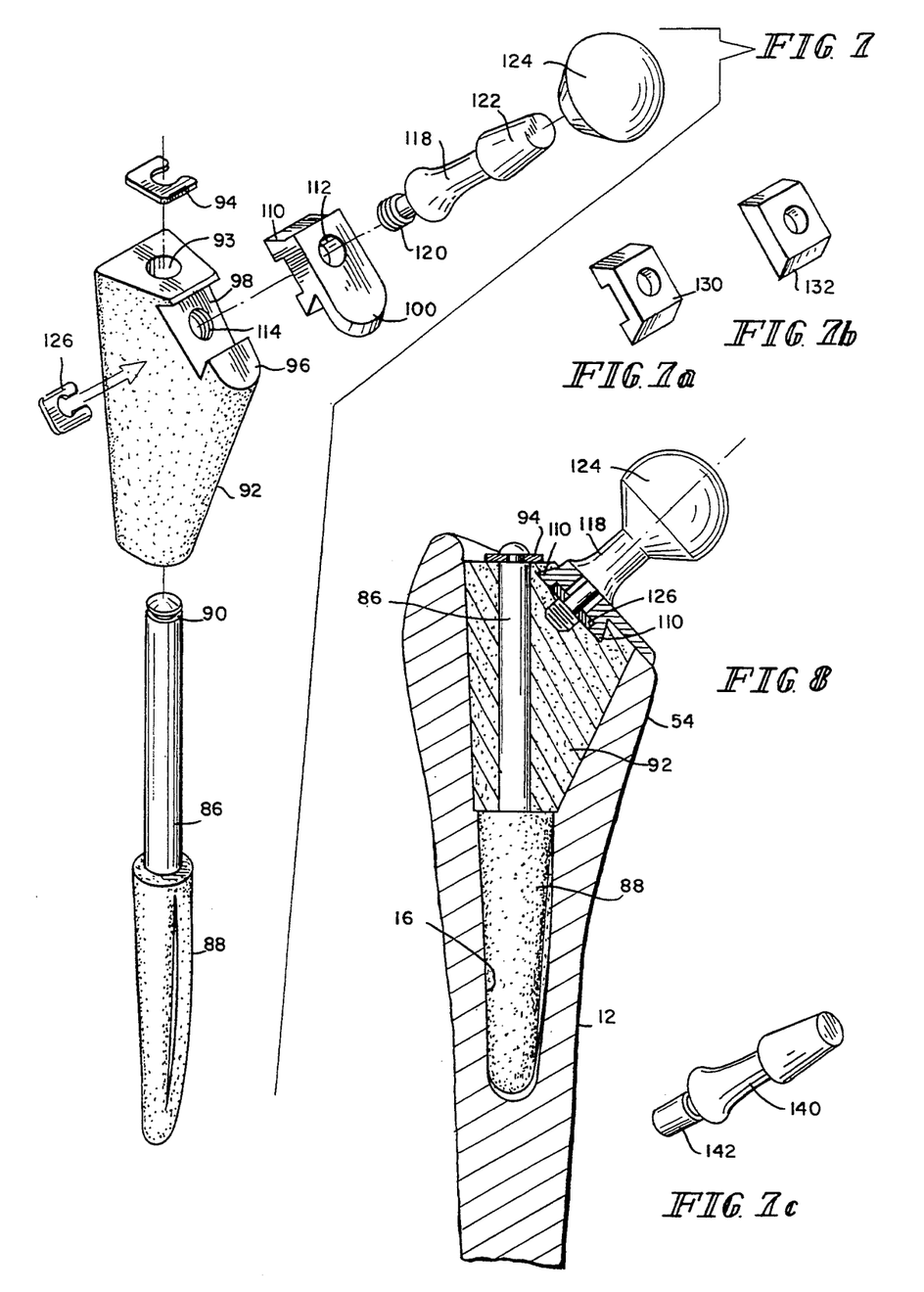
FIG. 7 is an exploded perspective view of another embodiment of the present invention showing a modified stem member and a modified neck and body member.
FIG. 7a is a perspective view of an adapter block for use when the collar component shown in FIG. 7 is not utilized.
FIG. 7b is a view similar to FIG. 7A showing a modified adapter block.
FIG. 7c is a perspective view of a modification of the neck member shown in FIG. 7.
FIG. 8 is a cross sectional view through the assembly illustrated in Fig. 7 installed in the femur.

FIG. 7 shows yet another embodiment of the present invention. In this embodiment, a stem member 86 is provided that includes a lower portion 88 that is coated with a bone-in growth porous metal coating. Bone-in growth coatings are known in the art, and it will be understood that this type of stem 86 is adapted to be inserted into a bone without the use of any grouting or cement material. The upper end of the stem 86 includes a groove 90 that is adapted to mate with a stem clip 94 after the stem member 86 has been inserted through a bore 93 in the body member 92. It will be understood that the groove 90 and the stem clip 94 function in a manner similar to the threaded end 28 and nuts 50, 64 shown in FIGS. 1–3 to secure the stem member 86 within the body member 92. The body member 92 includes a generally upwardly and inwardly (medially) facing surface 96 that is formed to include a generally trapezoid-shaped slot 98. A collar 100 is provided that includes a generally trapezoidal-shaped projection 110 that is configured to dovetail into the slot 98 to align and position the collar 100 in the body member 92. The collar 100 includes a hole 112 formed therethrough that aligns with a threaded hole 114 in the body member 92 when the collar 100 is mated with the body member 92.

FIG. 7 also shows a modified neck member 118 that includes a threaded end 120 and a tapered end 122. The neck member 118 is secured to the body member 92 by passing the threaded end 120 through the hole 112 in the collar 100 and into the threaded hole 114. A separate head member 124 is shown that is formed to include a tapered hole (not shown) that mates with the tapered end 122 of the neck member 118 to secure the head member 124 to the neck member 118. It will be understood that the neck member 118 and the head member 124 can be of various shapes and sizes other than those illustrated in FIG. 7. A collar clip 126 is shown that inserts under the projection 110 of the collar 100 to lock the neck member 118 in position after it has been screwed into the threaded hole 114 in the body member 92.

FIG. 7a shows an adapter block 130 that may be inserted into the slot 98 if the collar 100 (FIG. 7) is not used. The adapter block 130 is sized to fill the slot 98 so that the surface 96 on the body member 92 will be generally planar. The adapter block 130 shown in FIG. 7a is configured to accept the stem clip 126 as described above.

FIG. 7b shows another adapter block 132 that also may be inserted into the slot 98 if the collar 100 (FIG. 7) is not used. The adapter block 132 is sized To fill the slot 98 so that the surface 96 on the body member 92 will be generally planar. The adapter block 132 differs from the adapter block 130 in that block 132 is used when no stem clip 126 will be utilized.

FIG. 7c shows a modified neck member 140 that is similar to the neck member 118 shown in FIG. 7. Neck member 140 differs in that the threaded end 120 (FIG. 7) is replaced by a tapered end 142 that may be inserted into a tapered hole (not shown) in any of the body members, such as body member 92 (FIG. 7).

FIG. 8 shows the prosthesis of FIG. 7 assembled and in a use position. To assemble the embodiment shown in FIG. 7, the stem member 86 is first inserted through the bore 93 in the body member 92. The stem clip 94 is then engaged with the groove 90 to secure the stem member 86 within the body member 92. The collar 100 is then engaged with the body member 92 by sliding the projection 110 into the slot 98 so that the hole 112 aligns with the threaded hole 114. The neck member 118 is then threadingly engaged into the threaded hole 114 by the threaded end 120. After the neck member 118 is tightened, the collar clip 126 is inserted under the projection 110 to lock the neck member 118 in position. The head member 124 is then inserted over the tapered end 122 of the neck member 118 to secure the head member 124 to the neck member 118.

The assembled prosthesis is then inserted into the cavity 16 of the femur 12 so that the collar 100 extends over the Calcar portion 54. It will be understood that in this embodiment the cavity 16 is excavated only to the extent necessary to permit the assembled prosthesis to exactly fit within the cavity 16. As discussed previously, the lower portion 88 of the stem member 86 will be secured within the femur 12 by the natural growth process of the bone into the porous surface. Illustratively, the body member 92 may also be coated with a bone-in growth material to enhance this in growth process.

Although specific embodiments have been shown assembled in FIGS. 1–8, it will be understood that the components shown in the figures may be interchangeable, and a prosthesis may be assembled utilizing combinations of the illustrated components. This ability to select different sizes and shapes of components to assemble a prosthesis greatly enhances the flexibility available at the time of the operation. Thus, depending upon the anatomical indications presented by the patient, numerous combinations are available to assemble a prosthesis at the time of the operation to meet the exact requirements for that patient.

Although the invention has been described in detail with reference to preferred embodiments and specific examples, variations and modifications exist within the scope and spirit of the invention as described and defined in the following claims.

What is claimed is:

1. A kit for the assembly of a modular bone joint prosthesis for the replacement of a head, neck, and adjacent portions of a bone, the kit comprising
   at least two stems, with each stem sized for insertion into a cavity of the bone,
   at least two bodies, with each body sized to replace a portion of the bone, and with each body configured to be joined in fixed attachment to one of the at least two stems,
   at least two head members, with each head member sized to replace a head portion of the bone, and
   means for fixedly attaching one of the at least two head members to one of the at least two bodies.

2. The invention of claim 1 wherein the body is provided with a collar to engage a resected portion of said bone to assist in stabilizing said prosthesis relative to said bone.

3. The invention of claim 1 in which each of said body members is provided with a bore and in which each of said stems is provided with an upper portion to be received in a bore of one of said bodies to provide said fixed attachment between said body and said stem.

4. The invention of claim 3 further comprising means for attaching the upper portion of each stem to the body into which it is inserted.

5. The invention of claim 4 in which said attachment means is a threaded element for threadedly engaging the upper portion of said stem.

6. The invention of claim 4 in which said stem upper portion is provided with a groove and said attachment means is a clip for engaging said groove.

7. The invention of claim 1 in which at least one of said two bodies is at least partially covered with a porous metal coating to promote bone ingrowth to assist in stabilizing said prosthesis in said bone.

8. The invention of claim 3 in which at least one of said two stems is provided with an enlarged chamfer at the lower end of its upper portion to engage said body.

9. The invention of claim 1 in which each of said bodies is formed to provide a plane coinciding generally with a plane of resection of the joint and another plane at an angle with respect to the first said plane and located on said body overlying in part an axis of said stem.

10. The kit of claim 1 further comprising at least two collars, with each collar configured for positioning between one of the at least two bodies and one of the at least two head members so that the collar can increase stability of the assembled modular joint prosthesis.

11. The Kit of claim 1, wherein one of the at least two stems has a different size and shape as another of the at least two stems.

12. The Kit of claim 1, wherein one of the at least two bodies has a different size and shape as another of the at least two bodies.

13. The Kit of claim 11, wherein one of the at least two bodies has a different size and shape as another of the at least two bodies.

14. The Kit of claim 1, wherein one of the at least two head members has a different size and shape as another of the at least two head members.

15. The Kit of claim 11, wherein one of the at least two head members has a different size and shape as another of the at least two head members.

16. The Kit of claim 12, wherein one of the at least two head members has a different size and shape as another of the at least two head members.

17. The Kit of claim 13, wherein one of the at least two head members has a different size and shape as another of the at least two head members.

18. A kit for assembly of a hip prosthesis for replacement of a head, neck, and adjacent portions of a femur resected in a plane, the kit comprising:

at least two stem members having an upper portion and a lower portion, the lower portion sized to be received in a shaft of the femur, at least two body members sized to replace a portion of the femur and each body member configured so that any one of the at least two body members is receivable over said upper portion of any one of the at least two stem members and said body member having an upper surface defining a plane generally coincident with said resection plane, and at least two head members sized to replace the head of the femur and including means to attach any one of the at least two said head members to any one of said at least two body members adjacent said plane.

19. The invention of claim 18 further comprising a collar provided with each of said body members to engage said bone generally on said resected plane to assist in stabilizing said prosthesis relative to said bone.

20. The invention of claim 18 in which each said means to attach is a neck extending from its associated body transverse to said resected plane.

21. The invention of claim 18 comprising means for fastening each said body to the upper portion of the stem received by said body.

22. An implant system for replacing a portion of a femur, said femur having a neck and having a longitudinal cavity defining a first axis, the system comprising a plurality of components with each component being provided in various sizes and shapes, said components including at least two body members, each body member being formed to include a longitudinal bore that is generally aligned with said first axis and an upwardly and inwardly facing surface, at least two elongated stem members, each stem member having an upper portion and a lower portion, said lower portion configured to be received in said femur cavity and said upper portion configured to be received and secured in the bore of any one of the said at least two body members, and at least two head members, each head member being sized to replace a head of the femur, each head member being mounted on any one of said at least two bodies by a neck extending from said upwardly and inwardly facing surface, at least one of said at least two bodies having a porous metal surface for promoting bone ingrowth to assist in stabilizing said body in said femur, and further comprising fastening means for securing any one of said stem upper portions in any one of said body members bore.

23. The invention of claim 22 including a collar provided with each of said body members for engaging a resected portion of said femur to assist in stabilizing said prosthesis in said femur.

* * * * *

UNITED STATES PATENT AND TRADEMARK OFFICE
CERTIFICATE OF CORRECTION

PATENT NO.    : 5,370,706
DATED         : December 6, 1994
INVENTOR(S)   : Richard Bolesky and Todd S. Smith It is certified that error appears in the above-identified patent and that said Letters Patent is hereby corrected as shown below:

<u>Title page,</u>
Item [75], Inventor(s), should read: -- Richard Bolesky; Todd S. Smith; and Charles E. Whitcraft, Jr. all of Warsaw, Indiana --

Signed and Sealed this

Thirty-first Day of December, 2002

JAMES E. ROGAN
*Director of the United States Patent and Trademark Office*